United States Patent [19]
Murata et al.

[11] 3,943,169
[45] Mar. 9, 1976

[54] 3-(TRISUBSTITUTED BENZOYL)-PROPIONIC ACID

[75] Inventors: Tadakazu Murata, Suita; Akira Nohara, Kyoto; Hirosada Sugihara, Suita; Yasushi Sanno, Ikeda, all of Japan

[73] Assignee: Takeda Chemical Industries, Ltd, Osaka, Japan

[22] Filed: Sept. 12, 1972

[21] Appl. No.: 288,348

[30] Foreign Application Priority Data

| Sept. 13, 1971 | Japan | 46-71087 |
| Sept. 13, 1971 | Japan | 46-71088 |
| Dec. 29, 1971 | Japan | 47-3167 |
| Jan. 11, 1972 | Japan | 47-5401 |

[52] U.S. Cl. ........ 260/521 R; 260/340.3; 260/340.5; 260/340.6; 260/465 R; 260/465 D; 260/516; 424/278; 424/317
[51] Int. Cl.² .................. C07C 65/00; C07C 65/22
[58] Field of Search .................. 260/521 R

[56] References Cited
UNITED STATES PATENTS

| 2,720,542 | 10/1955 | Newhall | 260/521 |
| 3,502,679 | 3/1970 | Houlihan et al. | 260/521 R |
| 3,509,132 | 4/1970 | Houlihan | 260/521 R |
| 3,515,731 | 6/1970 | Conover | 260/473 F |

OTHER PUBLICATIONS

Sharma et al., J. Ind. Chem. Soc., 36, No. 2, 117, (1959).
Tatsuo Shoji, Chem. Abst., 54, 5587d.
Chakravarti et al., J. Indian. Chem. Soc., 44, 6, (1967).
Bargellini et al., C.A., 6, 2417⁶.
Widmer et al., C.A., 63, 1747b, (1965).
Tateishi et al., Tetrahedron, 27, 237, (1971).
Irani et al., C.A., 45, 1974e, (1951).
Dalal et al., C.A., 32, 526⁶.
Coillard et al., C.A., 48:5841h.
Davies et al., C.A., 50, 7760d.
Zymalkowski et al., Archiv. Pharm. 299(6), 545, (1966).
Momose et al., C.A., 50, 911.

*Primary Examiner*—John F. Terapane
*Attorney, Agent, or Firm*—Wenderoth, Lind & Ponack

[57] ABSTRACT

The present invention relates to a compound of the formula:

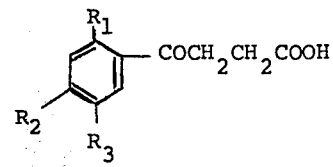

wherein $R_1$ is an alkyl group of 1 to 4 carbons, an alkoxy group of 1 to 4 carbons or hydroxyl, and $R_2$ and $R_3$ are either the same or different and may be an alkyl group of 1 to 4 carbons, an alkoxy group of 1 to 4 carbons, hydroxyl, halogen or an alkylthio group of 1 to 4 carbons, or they are, connecting with each other, an alkylenedioxy group of 1 to 3 carbons, with the proviso that when $R_1$ is an alkoxy group, at least one of $R_2$ and $R_3$ is an alkoxy group or an alkylthio group, or $R_2$ and $R_3$ are, connecting with each other, an alkylenedioxy group; when $R_1$ is an alkyl group or hydroxyl, $R_2$ and $R_3$ are the same or different and may be an alkoxy group, an alkylthio group or, connecting with each other, an alkylene dioxy group; when $R_2$ and $R_3$ are methoxy, $R_1$ is an alkyl group of 2 or 3 carbons, an alkoxy group of 2 to 4 carbons or hydroxyl, and when $R_2$ is methyl and $R_3$ is methoxy, $R_1$ is an alkoxy group of 2 to 4 carbons or its pharmaceutically acceptable salts. The present invention also provides for a method of preparing the aforementioned compounds. The present compounds are characterized by exhibiting strong spasmolytic or relaxing action on the gall bladder, the common biliary duct, as well as exhibiting strong choleric activity and low toxicity.

6 Claims, No Drawings

3-(TRISUBSTITUTED BENZOYL)-PROPIONIC ACID

This invention relates to a novel 3-(trisubstitued benzoyl)-propionic acid and the production thereof.

Heretofore, there has been no report that benzoyl propionic acid derivatives have spasmolytic or relaxing action of a gall bladder, the common biliary duct, especially Oddi's sphincter.

The present inventors have found that a compound represented by the following formula [I] has a strong spasmolytic or relaxing action on a gall bladder, the common biliary duct, especially Oddi's sphincter as well as a strong choleretic activity and a low toxicity:

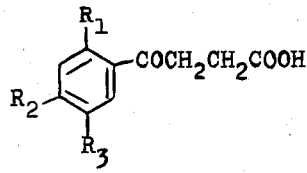

(I)

wherein $R_1$ is an alkyl group of 1 to 4 carbons, an alkoxy group of 1 to 4 carbons or hydroxyl, and $R_2$ and $R_3$ are, the same with or different from each other, an alkyl group of 1 to 4 carbons, an alkoxy group of 1 to 4 carbons, hydroxyl, halogen or an alkylthio group of 1 to 4 carbons or they are, connecting with each other, an alkylenedioxy group of 1 to 3 carbons, with the proviso that when $R_1$ is the alkoxy group, at least one of $R_2$ and $R_3$ is the alkoxy group or the alkylthio group or $R_2$ and $R_3$ are, connecting with each other, the alkylenedioxy, when $R_1$ is the alkyl group or hydroxyl, $R_2$ and $R_3$ are, the same or different, the alkoxy group, the alkylthio group or, connecting with each other, the alkylenedioxy, when $R_2$ and $K_3$ are methoxy, $R_1$ is an alkyl group of 2 or 3 carbons, an alkoxy group of 2 to 4 carbons or hydroxyl and when $R_2$ is methyl and $R_3$ is methoxy, $R_1$ is an alkoxy group of 2 to 4 carbons.

Referring to the formula [I], the alkyl group of $R_1$, $R_2$ or $R_3$ may be exemplified by methyl, ethyl, n-propyl, isopropyl, n-butyl, sec.butyl and tert. butyl, the alkoxy group of $R_1$, $R_2$ or $R_3$ may be exemplified by methoxy, ethoxy, n-propoxy, isopropoxy, n-butoxy, sec.butoxy and tert. butoxy, halogen atom of $R_2$ or $R_3$ may be exemplified by chlorine, bromine, iodine and fluorine, the alkylthio group of $R_2$ or $R_3$ may be exemplified by methylthio, ethylthio, n-propylthio, isopropylthio, n-butylthio, sec. butylthio and tert. butylthio and the alkylenedioxy group formed by connection of $R_2$ and $R_3$ may be exemplified by methylenedioxy, ethylenedioxy, propylenedioxy.

The compound of the formula [I] can be produced by, for example, 1. reacting a compound of the formula (II)

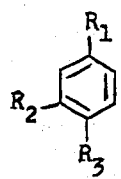

(II)

wherein $R_1$, $R_2$ and $R_3$ have the same meaning as defined above with a reactive derivative of succinic acid such as succinic anhydride, succinic acid half ester half halide, succinic acid half ester half nitrile or succinic acid half ester and hydrolysing the resultant, if necessary.

2. subjecting a compound of the formula [III]

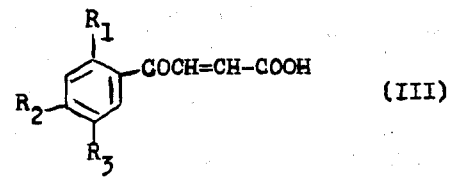

(III)

wherein $R_1$, $R_2$ and $R_3$ have the same meaning as defined above to hydrogenation, and 3. treating a compound of the formula [IV]

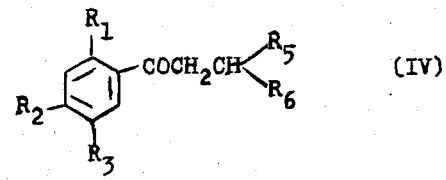

(IV)

wherein $R_1$, $R_2$ and $R_3$ have the same meaning as defined above and $R_5$ and $R_6$ are the same with or different from each other, esterified carboxyl group or cyano or one of $R_5$ and $R_6$ is hydrogen and the other is cyano with an acid or an alkali.

4. and the compound [I] wherein $R_1$ is hydroxyl, namely the compound of the formula

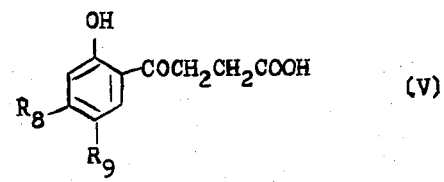

(V)

wherein $R_8$ and $R_9$ are, the same with or different from each other, an alkoxy group of 1 to 4 carbons, or an alkylthio group of 1 to 4 carbons, or connecting with each other, an alkylenedioxy group of 1 to 3 carbons can be produced by, for example, subjecting a compound of the formula [VI]

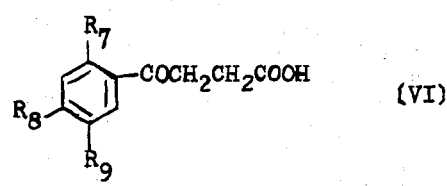

(VI)

wherein $R_7$ is an alkoxy group and $R_8$ and $R_9$ have the same meaning as above to ether cleavage reaction.

Esterified carboxyl group of $R_5$ and $R_6$ may be exemplified by alkoxycarbonyl (e.g. methoxycarbonyl, ethoxycarbonyl, etc.), aralkoxycarbonyl (e.g. benzyloxycarbonyl, phenethyloxycarbonyl, etc.) and aryloxycarbonyl(phenoxycarbonyl, tolyloxycarbonyl, etc.).

An alkoxy group of $R_7$, $R_8$ and $R_9$, an alkylthio group and an alkylenedioxy group of $R_8$ and $R_9$ may be exemplified by the same as those of $R_1$, $R_2$ and $R_3$.

A manner for the production of the compound [I] by the reaction between the compound [II] and the reactive derivative of succinic acid varies with the kinds of the reactive derivatives of succinic acid. Typical manners are as follows:

1-A. The reaction between the compound [II] and succinic anhydride gives directly the compound ]I].

(1-B. The reaction between the compound [II] and succinic acid half ester half halide such as β-methoxycarbopropionyl chloride and β-ethoxycarbopropionyl chloride or succinic acid half ester half nitrile such as methyl β-cyanopropionate and ethyl β-cyanopropionate gives the ester corresponding to the compound [I] and the hydrolysis of the ester gives the compound [I].

1-C. The reaction between the compound [II] and a succinic acid half ester such as monomethyl succinate and monoethyl succinate in the presence of polyphosphoric acid or polyphosphoric acid ester gives the ester corresponding to the compound [I], and the hydrolysis of the ester gives the compound [I].

The reaction of the above (1-A) or (1-B) is advantageously carried out in a suitable inert solvent such as aromatic hydrocarbon or its derivative (e.g. benzene, toluene, xylene, nitrobenzene), halogeno aliphatic hydrocarbon (e.g. methylene chloride, chloroform, carbon tetrachloride, ethylene dichloride, ethylene tetrachloride), ether (e.g. ethyl ether, propyl ether, isopropyl ether, ethyleneglycol dimethylether, ethyleneglycol diethylether and carbon disulfide, and the mixture of two or more of them. It is desirable to carry out the reaction under anhydrous conditions and in the presence of metal chloride such as anhydrous aluminum chloride, stannic chloride, zinc chloride and titanium tetrachloride and the mixture of two or more of them. The reaction temperature is, in general, $-70°$ to $200°C$ and desirably $-10°$ to $100°C$. The introduction of dry hydrogen chloride to the reaction system can serve to accelerate the desired reaction.

The reaction of the above (1-C) may conveniently be carried out in the absence of a solvent. In this reaction, any polyphosphoric acid or polyphosphoric acid ester can be employed and it may be used in an amount of, in general, 2 to 20 times, preferably 5 to 10 times as much as the compound [II]. The reaction temperature is, in general, $0°$ to $250°C$, desirably $30°$ to $100°C$. The other conditions may be the same with those of the reaction (1-A) or (1-B).

The reactions of (1-B) and (1-C) give the ester corresponding to the compound [I]. The ester, in the reaction mixture or isolated from the reaction mixture, is subjected to hydrolysis. The hydrolysis is carried out under acidic or alkaline conditions. In case of alkaline conditions, the hydrolysis may conveniently be carried out in the presence of water or a mixture of water and a lower alcohol such as methanol and ethanol in the presence of an alkaline substance such as sodium hydroxide or potassium hydroxide, sodium bicarbonate, sodium carbonate, potassium carbonate at the temperature ranging from about $-10°$ to $150°C$. In case of acidic condition, the hydrolysis may conveniently be carried out in water or the mixture of water and a lower alcohol such as methanol and ethanol, an ether such as tetrahydrofuran and dioxane or an organic acid such as formic acid and acetic acid in the presence of a mineral acid such as hydrochloric acid, sulfuric acid and phosphoric acid at a temperature ranging about $-10°$ to $150°C$. In the reaction of (1-C), after condensation reaction between the compound [II] and the succinic acid half ester is completed, polyphosphoric acid or polyphosphoric acid ester in the reaction mixture is hydrolized by addition of water and the hydrolysis of the ester of the compound [I] is easily carried out by addition of an aqueous organic solvent and heating the reaction mixture.

Hydrogenation of the reaction (2) mentioned above may be carried out in conventional manners such as catalytic reduction, a reduction using an acid with a metal such as zinc, iron or tin, or an amalgam such as sodium amalgam. Catalytic reduction is, in general, carried out in a suitable solvent such as a lower alcohol (e.g. methanol, ethanol), an ether (e.g. dioxane, tetrahydrofuran, isopropylether), acetic acid, ethyl acetate or water, or the mixture of one or more of them in the presence of catalyst such as palladium, platinum, rhodium, and nickel.

The compound [III] is a novel compound and it may be produced by reacting the compound [II] with a reactive derivative of maleic acid, for instance, maleic anhydride in a manner similar to that of (1-A). (1-B) or (1-C).

Treatment of the compound [IV] with a acid or an alkali can be carried out in conditions similar to those of hydrolysis of the ester in the reaction (1-B) or (1-C).

Ether cleavage of the compound [VI] is carried out in the presence of an inorganic acid e.g. hydroiodic acid, hydrobromic acid, hydrochloric acid, the mixture of potassium iodide and polyphosphoric acid, an organic acid such as formic acid, acetic acid, trifluoroacetic acid and the mixture of the organic acid and sodium iodide or potassium iodide. In addition to the acid, a suitable solvent such as water, a lower alcohol, a phenol, an organic acid, an ether such as dioxane and tetrahydrofuran may be employed. The reaction temperature ranges, in general, from $0°$ to $200°C$, desirably $70°$ to $160°C$.

In order to isolate the desired compound [I] from any of reaction mixtures among those described above, any conventional manner may be employed. For example, steam distillation, extraction with a solvent or an alkaline solution, distillation or chromatography are advantageously employed.

The compound [I] may be obtained in the form of pharmaceutically acceptable salt, such as metal salt with e.g. sodium, calcium, magnecium, lithium, ammonium salt or amine salt.

The compound [I] thus produced is novel one and has strong spasmolytic or relaxing action on smooth muscles of a gall bladder, the common biliary duct, especially Oddi's sphincter as well as strong choleretic activity and low toxicity and therefore it is very useful as a therapeutic agent for cholerystopathy, especially biliary dyskinesia and cholelithiasis, or cholagogus.

The compound [I] can be administered orally in the form of tablet, granules, powder, or by way of injection.

Typical effective daily dose of the compound [I] is, usually about 20 to 1000 mg, desirably, 50 to 300 mg. when administered intravenously to adult human. Of course, an increased or reduced dose is also effective depending on symptoms.

In the following examples, the relationship between parts by weight and parts by volume corresponds to the relationship between gram and milliliter.

EXAMPLE 1

To a mixture of 7.5 parts by weight of 1,2,4 -triethoxybenzene, 40 parts by volume of tetrachloroethane and 7.5 parts by weight of succinic anhydride is added 23 parts by weight of anhydrous aluminum chloride and the mixture is stirred for 1 hour at 25°C and for another 2 hours at 60°C. After addition of 50 parts by weight of ice and 50 parts by volume of concentrated hydrochloric acid, the reaction mixture is subjected to steam distillation. After cooling crystals separated from the remaining liquid are collected by filtration and recrystallized from aqueous ethanol, whereby 2.5 parts by weight of 3-(2',4',5'-triethoxybenzoyl)-propionic acid is obtained as colorless needles. m.p. 150°–151°C.

EXAMPLES 2 to 4

According to a manner similar to that of Example 1, the following compounds are obtained.

| Example No. | Compound | mp. (°C) |
|---|---|---|
| 2 | 3-(2'-ethoxy-4',5'-dimethoxybenzoyl)-propionic acid | 156–158 |
| 3 | 3-(2'-n-butoxy-4',5'-dimethoxybenzoyl)-propionic acid | 156–157 |
| 4 | 3-(2',4',5'-tri-n-butoxybenzoyl)-propionic acid | 117–118 |

EXAMPLE 5

To the mixture of 9.0 parts by weight of 3,4-diethoxytoluene, 6.0 parts by weight of succinic anhydride and 100 parts by volume of carbon tetrachloride is added 27 parts by weight of anhydrous aluminum chloride. The mixture is stirred for 1 hour at 25°C and mildly refluxed for 2 hours. After cooling, 70 parts by weight of ice and 70 parts by volume of concentrated hydrochloric acid are added to the mixture and thereto is further added methylenedichloride and the whole mixture is shaken. The organic solvent layer is separated and extracted with a 2N-aqueous solution of sodium carbonate. The aqueous solution is adjusted with diluted hydrochloric acid to pH 2.5, whereby 3-(2'-methyl-4',5'-diethoxybenzoyl)-propionic acid is obtained as crystals. Recrystallization of the crystals gives 10.0 parts by weight of colorless plates melting at 116°–117°C.

EXAMPLES 6–14

According to a similar manner to that of Example 5, the following compounds are produced.

| Example No. | Compound | mp. (°C) |
|---|---|---|
| 6 | 3-(2',4'-dimethoxy-5'-chlorobenzoyl)-propionic acid | 185–187 |
| 7 | 3-(2'-n-propyl-4',5'-dimethoxybenzoyl)-propionic acid | 95–96 |
| 8 | 3-(2'-n-propyl-4'-methoxy-5'-ethoxybenzoyl)-propionic acid | 93 |
| 9 | 3-(2'-n-propyl-4'-methoxy-5'-n-propoxybenzoyl)-propionic acid | 70 |
| 10 | 3-(2'-n-propyl-4'-methoxy-5'-n-butoxybenzoyl)-propionic acid | 85–86 |
| 11 | 3-(2',4'-diethoxy-5'-chlorobenzoyl)-propionic acid | 172–173 |
| 12 | 3-(2'-methoxy-4'-t.-butyl-5'-ethoxybenzoyl)-propionic acid | 135–137 |
| 13 | 3-(2',4'-diethoxy-5'-ethylbenzoyl)-propionic acid | 153–155 |
| 14 | 3-(2'-methoxy-4'-chloro-5'-methoxybenzoyl)-propionic acid | 186–188 |

EXAMPLE 15

To the mixture of 13.6 parts by weight of 1-ethoxy-3,4-dimethoxybenzene, 12 parts by weight of β-ethoxycarbopropionyl chloride and 65 parts by volume of benzene is added 18 parts by weight of anhydrous stannic chloride over 25 minutes and the mixture is stirred at 25°C for 1 hour. The mixture is cooled at 5°C and 130 parts by volume of 20% hydrochloric acid is added thereto on stirring. To the mixture is added 250 parts by volume of methylene chloride and shaken. The methylene chloride layer is separated and extracted with a 5% aqueous solution of sodium bicarbonate twice and then washed with water twice. After drying with anhydrous calcium chloride, the solvent is distilled off.

To the residue are added 120 parts by volume of methanol and 95 parts by volume of 1N-methanolic potassium hydroxide. The mixture is stirred at 60°C for 1 hour. After removal of methanol by distillation under reduced pressure, to the residue are added 150 parts by volume of water and 100 parts by volume of methylene chloride, and the mixture is shaken. The aqueous layer is separated and adjusted to pH 2.5 with concentrated hydrochloric acid, whereby 14 parts by weight of 3-(2'-ethoxy-4',5'-dimethoxybenzoyl)-propionic acid as pale yellow crystals. mp. 156°–158°C.

EXAMPLES 16–23

After a manner similar to that of Example 15, the following compounds are obtained.

| Example No. | Compound | mp. (°C) |
|---|---|---|
| 16 | 3-(2',4',5'-triethoxybenzoyl)-propionic acid | 150–151 |
| 17 | 3-(2'-n-butoxy-4',5'-dimethoxybenzoyl)-propionic acid | 156–157 |
| 18 | 3-(2'-methoxy-4',5'-methylenedioxybenzoyl)-propionic acid | 140–141 |
| 19 | 3-(2'-n-propyl-4',5'-methylenedioxybenzoyl)-propionic acid | 138–139 |
| 20 | 3-(2'-n-propyl-4'-methoxy-5'-n-butoxybenzoyl)-propionic acid | 85–86 |
| 21 | 3-(2'-ethoxy-4'-methyl-5'-methylthiobenzoyl)-propionic acid | 117–118 |
| 22 | 3-(2'-methoxy-4'-chloro-5'-methoxybenzoyl)-propionic acid | 186–188 |
| 23 | 3-(2'-methoxy-4'-t.-butylbenzoyl-5'-ethoxy)-propionic acid | 135–137 |

EXAMPLE 24

In 30 parts by volume of dried ethylether are dissolved 3.0 parts by weight of 1,2,4-triethoxybenzene and 3.0 parts by weight of methyl β-cyanopropionate. To the solution are added 2.0 parts by weight of anhydrous zinc chloride and 2.0 parts by weight of anhydrous aluminum chloride. Hydrogen chloride gas is passed through the mixture over 30 minutes. The mixture is left standing at 15°C for 15 hours and 100 parts by volume of ethylether is added thereto. After removal of the upper layer, the residue is mixed with 100 parts by volume of 20% hydrochloric acid and refluxed for 30 minutes whereby pale yellow crystals are separated. After cooling the crystals are collected by filtration (yield: 4.3 parts).

The crystals thus obtained is mixed with 30 parts by volume of methanol and 50 parts by volume of 1N-methanolic potassium hydroxide and heated for 40 minutes. After removal of the solvent, the remaining liquid is dissolved in 70 parts by volume of water and neutralized with concentrated hydrochloric acid, whereby 3.0 parts by weight of 3-(2',4',5'-triethoxybenzoyl)-propionic acid is obtained as crystals melting at 150°–151°C.

EXAMPLE 25

According to a similar manner to that of Example 24, 3-(2',4',5'-tri-n-butoxybenzoyl)-propionic acid is obtained as colorless crystals melting at 117°–118°C.

EXAMPLE 26

A mixture of 12 parts by weight of 3,4-diethoxytoluene, 10 parts by weight of succinic acid monoethyl ester and 100 parts by weight of polyphosphoric acid is heated at 50°C for 1 hour. To the mixture is added 200 parts by volume of ice-water and the mixture is extracted with ethylether. By distilling off the solvent 15 parts by weight of ethyl 3-(2'-methyl-4',5'-diethoxybenzoyl)-propionate is obtained as crystals melting at 81°–82°C.

The crystals are added to a mixture of 70 parts by volume of methanol and 70 parts by volume of 1N-methanolic potassium hydroxide and heated at 50°C for 1 hour. After removal of methanol, the remaining liquid is dissolved in water and neutralized with concentrated hydrochloric acid, whereby 3-(2'-methyl-4',5'-diethoxybenzoyl)-propionic acid is obtained as crystals. Recrystallization from aqueous methanol gives 12 parts by weight of colorless platelets melting at 116°–117°C.

EXAMPLES 27–32

According to a similar manner to that of Example 26, the following compounds are obtained.

| Example No. | Compound | mp. (°C) |
| --- | --- | --- |
| 27 | 3-(2'-methoxy-4'-t.-butyl-5'-ethoxybenzoyl)-propionic acid | 135–137 |
| 28 | 3-(2'-n-propyl-4'-methoxy-5'-n-propoxybenzoyl)-propionic acid | 70 |
| 29 | 3-(2',4',5'-tri-n-butoxybenzoyl)-propionic acid | 117–118 |
| 30 | 3-(2'-methoxy-4',5'-methylenedioxybenzoyl)-propionic acid | 140–141 |
| 31 | 3-(2'-n-butoxy-4',5'-dimethoxybenzoyl)-propionic acid | 156–157 |
| 32 | 3-(2',5'-diethoxy-4'-methylbenzoyl)-propionic acid | 128–129 |

EXAMPLE 33

To a 50% (weight/volume) chloroform solution of polyphosphoric acid ester are added 5 parts by weight of 1,2,4-triethoxybenzene and 3 parts by weight of succinic acid half methyl ester. The mixture is heated at 50°C for 1 hour and mixed with 50 parts by volume of ice-water and 30 parts by volume of chloroform and then stirred for 40 minutes at 26°C.

The chloroform layer is separated and washed with water and dried. The solvent is distilled off. To the residue is added 30 parts by volume of methanol and 30 parts by volume of 1N-methanolic potassium hydroxide. The mixture is stirred for 40 minutes at 50°C and the solvent is distilled off. The residue is dissolved in 100 parts by volume of water and washed with 30 parts by volume of diethylether. The pH of the mixture is adjusted to 2.5 with concentrated hydrochloric acid whereby 3-(2',4',5'-triethoxybenzoyl)-propionic acid is obtained as crystals. Recrystallization of the crystals from aqueous acetone gives 4.1 parts by weight of colorless plates melting at 150°–151°C.

EXAMPLE 34

To a mixture of 2.1 parts by weight of 1,2,4-triethoxybenzene, 1.2 part by weight of maleic anhydride and 30 parts by volume of carbon tetrachloride is added 5.2 parts by weight of anhydrous aluminum chloride. The mixture is stirred for 1 hour and heated at 50°C for another 1 hour. After cooling, concentrated hydrochloric acid and ice are added to the mixture. The mixture is extracted with methylenechloride and the methylenechloride layer is washed with water and dried over anhydrous sodium sulfate. Upon removing the solvent by distillation, 3-(2',4',5'-triethoxybenzoyl)-trans-acrylic acid is obtained as crystals. Recrystallization from a mixture of ethanol and benzene gives yellow needles melting at 192°–194°C.

A mixture of 1.0 part by weight of 3-(2',4',5'-triethoxybenzoyl)-trans-acrylic acid, 50 parts by volume of methanol and 0.2 part by weight of 5% palladium-charcoal is subjected to catalytic reduction at 25°C under atmospheric pressure for 1 hour. After removal of the catalyst by filtration, the filtrate is evaporated and the residue is recrystallized from aqueous ethanol to give 0.85 part by weight of 3-(2',4',5'-triethoxybenzoyl)-propionic acid as pale yellow needles melting at 150°–151°C.

EXAMPLES 35–38

According to a similar manner to that of Example 34, the following starting 3-(trisubstituted benzoyl)-acrylic acids and the objective 3-(trisubstituted benzoyl)-propionic acids are obtained.

| Example No. | Starting compound Compound | mp(°C) | Catalyst | Objective compound Compound | mp(°C) |
|---|---|---|---|---|---|
| 35 | 3-(2'-methyl-4',5'-diethoxy-benzoyl)-trans-acrylic acid | 126–127.5 | Pd-C | 3-(2'-methyl-4',5'-diethoxy-benzoyl)-propionic acid | 116–117 |
| 36 | 3-(2',4'-diethoxy-5'-chloro-benzoyl)-trans-acrylic acid | 198 | Na-amalgam | 3-(2',4'-diethoxy-5'-chloro-benzoyl)-propionic acid | 172–173 |
| 37 | 3-(2'-n-propyl-4'-methoxy-5'-n-butoxy-benzoyl)-trans-acrylic acid | 91–93 | Pd-C | 3-(2'-n-propyl-4'-methoxy-5'-n-butoxy-benzoyl)-propionic acid | 85–86 |
| 38 | 3-(2'-n-propyl-4'-methoxy-5'-n-butoxy-benzoyl)-cis-acrylic acid | 103–106 | Pd-C | 3-(2'-n-propyl-4'-methoxy-5'-n-butoxy-benzoyl)-propionic acid | 85–86 |

EXAMPLE 39

To a mixture of 0.56 part by weight of diethyl malonate, 0.2 part by weight of 50% sodium hydride and 8.0 parts by volume of dried tetrahydrofuran is added 1.0 part by weight of 2',4',5'-triethoxyphenacyl chloride little by little at 25°C, and is stirred for 10 hours. To the mixture are added 8 parts by volume of ethyl acetate and 50 parts by weight of ice-water and shaken. The ethyl acetate layer is separated and washed with water and then dried and evaporated. The residue is recrystallized from methanol to give ethyl 3-(2', 4',5'-triethoxybenzoyl)-2-ethoxycarbopropionate as pale yellow plates melting at 97°–98°C.

A mixture of 1.5 part by weight of ethyl 3-(2',4',5'-triethoxybenzoyl)-2-ethoxycarbopropionate, 30 parts by volume of dioxane and 30 parts by volume of 30% sulfuric acid is heated at 120°C for 2 hours. The mixture is diluted with water and extracted with chloroform. The chloroform layer is separated and washed with water and dried. The solvent is distilled off, whereby 1.1 part by weight of 3-(2',4',5'-triethoxybenzoyl)-propionic acid is obtained. Recrystallization from aqueous methanol gives pale yellow needles melting at 150°–151°C.

EXAMPLE 40

According to a similar manner to that of Example 39, 2.0 parts by weight of 2',4',5'-triethoxyphenacylchloride is reacted with 0.9 part by weight of ethyl cyanacetate and 0.34 part by weight of 50% sodium hydride. The reaction mixture is subjected to chromatography with silica gel and eluted with benzene whereby 0.62 part by weight of 3-(2',4',5'-triethoxybenzoyl)-2-ethoxycarbopropionitrile is obtained as crystalls. Recrystallization from methanol gives colorless plates melting at 109°–110°C.

One part by weight of 3-(2',4',5'-triethoxybenzoyl)-2-ethoxycarbopropionitrile is treated with 14 parts by volume of 4N-hydrochloric acid and 40 parts by volume of acetic acid at 100°–110°C for 2 hours. The reaction mixture is treated according to the same manner as that of Example 39 whereby 0.65 part by weight of 3-(2',4',5'-triethoxybenzoyl)-propionic acid is obtained. mp. 150°–151°C.

EXAMPLE 41

To a mixture of 5.0 parts by weight of 3-methoxy-4-n-butoxy-n-propylbenzene, 4.0 parts by weight of β-chloropropionyl chloride and 20 parts by volume of dried benzene is added dropwise 9.0 parts by weight of stannic chloride dissolved in 5 parts by volume of carbon tetrachloride on cooling below 20°C. After stirring for 2 hours, about 200 parts by volume of ice-water is added to the mixture and thereto is added 200 parts by volume of benzene and then the mixture is shaken. The benzene layer is separated and washed with water and dried. The solvent is distilled off and the residue is crystallized from petroleum ether whereby ω-chloro-(2'-n-propyl-4'-methoxy-5'-n-butoxy)-propiophenone is obtained as colorless prisms. m.p. 42°–43°C To 30 parts by volume of dimethylsulfoxide is added 6.0 parts by weight of ω-chloro-2'-n-propyl-4'-methoxy- 5'-n-butoxy)-propiophenone. To the mixture added 1.0 part by weight of sodium cyanide. The mixture is stirred for 2 hours at 80°C. The reaction mixture is mixed with ice-water and extracted with benzene. The benzene layer is washed with water and dried. The solvent is distilled off and the residue is crystallized from aqueous ethanol to give 3-(2'-n-propyl-4'-methoxy-5'-n-butoxybenzoyl)-propionitrile is obtained as colorless needles melting at 76°C.

A mixture of 1 part by weight of 3-(2'-n-propyl-4'-methoxy-5'-n-butoxybenzoyl)-propionitrile, 2 parts by volume of concentrated hydrochloric acid, 5 parts by volume of water and 5 parts by volume of acetic acid is stirred for 1.5 hour at 80°–90°C. The reaction mixture is diluted with water and extracted with methylenechloride and the extract is washed, dried and concentrated. The residue is mixed with n-hexane and cooled whereby 0.8 part by weight of 3-(2'-n-propyl-4'-methoxy-5'-n-butoxybenzoyl)-propionic acid is obtained as crystals. Recrystallization from a mixture of methylenechloride and n-hexane gives pale yellow crystals melting at 85°–86°C.

EXAMPLE 42

A mixture of 2 parts by weight of 3-(2',4',5'-triethoxybenzoyl)-propionic acid, 12 parts by weight of potassium iodide and 60 parts by volume of formic acid is refluxed for 3 hours and the solvent is distilled off. The residue is mixed with 50 parts by volume of water and stirred for a while and then insoluble substance is collected by filtration. The substance is washed with water and recrystallized from aqueous ethanol whereby 1.2 part by weight of 3-(2'-hydroxy-4',5'-diethoxybenzoyl)-propionic acid is obtained as colorless crystals melting at 142°–144°C.

EXAMPLES 43–45

According to a similar manner to that of Example 42, the following compounds are obtained.

| Example No. | Compound | mp. (°C) |
| --- | --- | --- |
| 43 | 3-(2'-hydroxy-4',5'-dimethoxybenzoyl)-propionic acid | 162–163 |
| 44 | 3-(2'-hydroxy-4',5'-methylenedioxybenzoyl)-propionic acid | 180–182 |
| 45 | 3-(2'-hydroxy-4',5'-n-butoxybenzoyl)-propionic acid | 127 |

EXAMPLE 46

In 50 parts by volume of ethyl acetate are dissolved 9 parts by weight of 2-methyl-4,5-diethoxyacetophenone and 12 parts by weight of cupric bromide and the mixture is refluxed for 30 minutes. After removal of white inorganic substance by filtration, the filtrate is washed with water and dried over anhydrous sodium sulfate and the solvent is distilled off. The residue is recrystallized from petroleum ether to give 8.6 parts by weight of 2'-methyl-4',5'-diethoxyphenacylbromide as colorless crystals.

To a mixture of 15 parts by volume of dry tetrahydrofuran, 0.6 part by weight of diethyl malonate and 0.22 part by weight of sodium hydride is added 0.7 part by weight of 2'-methyl-4',5'-diethoxyphenacylbromide and the mixture is stirred for 12 hours. The reaction mixture is poured into water and acidified with diluted hydrochloric acid and extracted with ethyl acetate. The extract is washed with water, dried over anhydrous sodium sulfate, and the solvent is distilled off, whereby 0.68 part by weight of ethyl 3-(2'-methyl-4',5'-diethoxybenzoyl)-2-ethoxycarbopropionate is obtained as oily substance. The substance shows the following IR absorption and NMR spectrum.

IR absorption: $\nu_{max}^{Film}$ cm$^{-1}$ 1750–1715 (ester), 1665 (ketone)

NMR spectrum (60MC, in CDCl$_3$, δ, p.p.m.): 1.1–1.6 (12H, triplet, —CH$_2$—C$\underline{H}_3$), 2.42 (3H, singlet, aromatic C$\underline{H}_3$), 3.35 (2H, doublet, —COC$\underline{H}_2$—), 3.6–4.4 (9H, quartet and multiple, —C$\underline{H}_2$—CH$_3$ and —C$\underline{H}$-(COOC$_2$H$_5$)$_2$), 6.62 (1H, singlet, C'$_3$—$\underline{H}$), 7.28 (1H, singlet, C'$_6$—$\underline{H}$)

According to a similar manner to that of Example 39, 3-(2'-methyl-4',5'-diethoxybenzoyl)-propionic acid is obtained from ethyl 3-(2'-methyl-4',5'-diethoxybenzoyl)-2-ethoxycarbopropionate.

EXAMPLES 47–49

According to a similar manner to that of Example 41, the following starting 3-(trisubstituted benzoyl)-propionitriles and the objective 3-(trisubstituted benzoyl)-propionic acids are obtained.

| Example No. | Starting Compound | mp(°C) | Objective compound | mp(°C) |
| --- | --- | --- | --- | --- |
| 47 | 3-(2',4',5'-triethoxybenzoyl)-propionitrile | 117–118 | 3-(2',4',5'-triethoxybenzoyl)-propionic acid | 150–151 |
| 48 | 3-(2',4'-diethoxy-5'-chlorobenzoyl)-propionitrile | 141–142 | 3-(2',4'-diethoxy-5'-chlorobenzoyl)-propionic acid | 172–173 |
| 49 | 3-(2'-ethoxy-4'-methyl-5'-methythiobenzoyl)-propionitrile | 99–100 | 3-(2'-ethoxy-4'-methyl-5'-methylthio)-propionic acid | 117–118 |

What is claimed is:

1. A compound which is 3-(2',4',5'-triethoxybenzoyl)-propionic acid.
2. A compound which is 3-(2'-methyl-4',5'-diethoxybenzoyl)-propionic acid.
3. A compound which is, 3-(2'-n-propyl-4'-methoxy-5'-ethoxybenzoyl)-propionic acid.
4. A compound which is, 3-(2',4'-dimethoxy-5'-chlorobenzoyl)-propionic acid.
5. A compound which is, 3-(2',5'-dimethoxy-4'-chlorobenzoyl)-propionic acid.
6. A compound which is, 3-(2'-hydroxy-4',5'-diethoxybenzoyl)-propionic acid.

* * * * *